US008026353B2

(12) United States Patent
Kwon

(10) Patent No.: US 8,026,353 B2
(45) Date of Patent: Sep. 27, 2011

(54) NUCLEIC ACID MOLECULES ENCODING HUMAN 4-1BB

(75) Inventor: Byoung S. Kwon, Metairie, LA (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 3399 days.

(21) Appl. No.: 10/027,199

(22) Filed: Dec. 20, 2001

(65) Prior Publication Data
US 2002/0168719 A1 Nov. 14, 2002

Related U.S. Application Data

(60) Continuation of application No. 08/955,572, filed on Oct. 22, 1997, now abandoned, which is a continuation of application No. 08/461,652, filed on Jun. 5, 1995, now abandoned, which is a division of application No. 08/122,796, filed on Sep. 16, 1993, now abandoned.

(51) Int. Cl.
C07H 21/04 (2006.01)
C12P 21/06 (2006.01)
C12N 1/20 (2006.01)
C12N 5/00 (2006.01)
C12N 5/02 (2006.01)
C12N 15/74 (2006.01)

(52) U.S. Cl. .................. 536/23.5; 435/69.1; 435/320.1; 435/325; 435/471

(58) Field of Classification Search .................. 435/69.1, 435/252.3, 320.1, 471; 536/23.5
See application file for complete search history.

(56) References Cited

U.S. PATENT DOCUMENTS

| 4,560,649 A | 12/1985 | Saxena et al. | 435/7 |
| 5,350,836 A | 9/1994 | Kopchick et al. | 530/399 |
| 5,674,704 A | 10/1997 | Goodwin et al. | 435/69.1 |
| 5,928,893 A | 7/1999 | Cang | 435/69.1 |
| 7,211,259 B1 * | 5/2007 | Goodwin et | 424/185.1 |

FOREIGN PATENT DOCUMENTS

| WO | WO 95/07984 | 3/1995 |
| WO | WO 99/36093 | 7/1999 |

OTHER PUBLICATIONS

In: Biochemical Organic Compounds: Diagnostic Reagents, Product Catalog, Sigma Chemical Company, Product No. L1512, p. 1419, (1992).
"GenBank Accession No. L12964", (1993).
Alderson, M.R., et al., "Molecular and Biological Characterization of Human 4-1BB and its Ligand", Eur. J. Immunol., 24, pp. 2219-2227, (1994).
Armitage, R.J., "Identification of a source of biologically active CD40 ligand", Eur. J. Immunol, vol. 22, 2071-2076, (1992).

Chalupny, N.J., et al., "T-cell activation molecule 4-1BB binds to extracellular matrix proteins", Proc. Natl. Acad. Sci. USA, vol. 89,, pp. 10360-10364, (Nov. 1992).
Ellenhorn, J.D., et al., "In Vivo Administration of Anti-CD3 Prevents Malignant Progressor Tumor Growth", Science, vol. 242, 569-571, (Oct. 28, 1988).
Kwon, B.S., et al., "cDNA sequences of two inducible T-cell genes", Proceedings of the National Academy of Sciences, 86 (6), pp. 1963-1967, (Mar. 1989).
Leach, D.P., et al., "Enhancement of antitumor Immunity by CTLA-4 Blockade", Science, vol. 271, 1734-1736, (Mar. 22, 1996).
Linsley, P.S., "Immunosuppresion in Vivo by a Soluble Form of the CTLA-4 T Cell Activation Molecule", Science, vol. 257, 792-795, (Aug. 7, 1992).
Loo, D.T., et al., "Analysis of 4-1BBL and Laminin binding to murine 4-1BB, a member of the tumor necrosis factor receptor superfamily, and comparison with human 4-1BB", J. Biol. Chem., 272 (10), Not really a final rejection action but an Advisory Action, 6448-6456, (1997).
Mathews, L.S., "Expression Cloning of an Activin Receptor, a Predicted Transmembrane Serine Kinase", Cell, vol. 65, 973-982, (Jun. 14, 1991).
Melero, I., et al., "Monoclonal Antibodies Against the 4-1BB T-cell Activation Molecule Eradicated Established Tumors", Nature Medicine, 3 (6), pp. 682-685, (Jun. 1997).
Pollok, K., et al., "4-1BB T-Cell Antigen Binds to Mature B Cells and Macrophages, and Costimulates Pre-activated Splenic B Cells", J. Immunol., vol. 150, 275A, (May 1993).
Pollok, K.E., et al., "4-1BB T-cell antigen binds to mature B cells and macrophages, and costimulates anti-u-primed splenic B cells", Eur. J. Immunol., 24, 367-374, (1994).
Pollok, K.E., et al., "Inductible T Cell Antigen 4-1BB", J. Immunol., 150 (3), pp. 771-781, (1993).
Schwarz, et al., "Nucleotide sequence of ILA, a cDNA encoding a new member of the human nerve growth factor/tumor necrosis factor receptor family", Accession No. L12964, GenBank CD-ROM release, (Jun. 1993).
Schwarz, H., et al., "A receptor induced by lymphocyte activation (ILA): a new member of the human nerve-growth-factor/tumor-necrosis-factor receptor family", Gene, 134, 295-298, (1993).

(Continued)

Primary Examiner — Robert Landsman
(74) Attorney, Agent, or Firm — Barnes & Thornburg LLP

(57) ABSTRACT

The human receptor H4-1BB has been isolated, sequenced and disclosed herein. The cDNA of the human receptor H4-1BB is about 65% homologous to the mouse cDNA 4-1BB and was isolated by using probes derived from cDNA 4-1BB. A fusion protein for detecting cell membrane ligands to human receptor protein H4-1BB was developed. It comprises the extracellular portion of the receptor protein H4-1BB and a detection protein (alkaline phosphatase) bound to the portion of the receptor protein H4-1BB. B-cells that have expressed a ligand to receptor protein H4-1BB can be treated with cells that have expressed receptor protein H4-1BB and B-cell proliferation may be induced. The use of H4-1BB to block H4-1BB ligand binding has practical application in the suppression of the immune system during organ transplantation. A monoclonal antibody against H4-1BB can be used to enhance T-cell proliferation by treating T-cells that have expressed receptor protein H4-1BB with the anti H4-1BB monoclonal antibody. Tumors transfected with H4-1BBL may be capable of delivering antigen-specific signals as well as the co-stimulatory signals and can be killed by human cytotoxic T lymphocytes.

4 Claims, 6 Drawing Sheets

OTHER PUBLICATIONS

Sica, G., et al., "Modulation of the Immune Response Through 4-1BB", *Cancer Gene Therapy: Pact Achievements and Future Challenges*, 355-362 (2000).

Smith, C.A., "A Receptor for Tumor Necrosis Factor Defines an Unusual Family of Cellular and Viral Proteins", *Science*, vol. 248, 1019-1023, (May 25, 1990).

Strome, S.E., et al., "Enhanced Therapeutic Potential of Adoptive Immunotherapy by in Vitro CD28/4-1BB Costimulation of Tumor-Reactive T Cells Against a Poorly Immunogenic, Major Histocompatibility Complex Class I-Negative A9P Melanoma", *Journal of Immunotherpay 23*, 430-437, (2000).

Townsend, S.E., et al., "Tumor Rejection After Direct Costimulation of CD*+ T Cells by B7-Transfected Melanoma Cells", *Science*, vol. 259, 368-370, (Jan. 15, 1993).

Zhou, et al., "Characterization of Human Homologue of 4-1BB and its Ligand", *Immunol. Lett.*, 45, 67-73, (1995).

Biffen et al., "The CD45 tyrosine phosphatase regulates specific pools of antigen receptor-associated $p59^{fun}$ and CD4-associated $p56^{lck}$ tyrosine knases in human T-cells", EMBO J. 1994 13:1920-1994.

Brown et al., "A Family of Small Inducible Proteins Indicators of Various Activation Process", J. Immun. 1989 679-687.

Bressler et al., J. Immunol. 1991 147:2290-2294.

Broxmeyer et al., "Enhancing and suppressing effects of combinant murine macrophage inflammatory proteins on colony formation in vitro bone marrow myeloid progenitor cells", Blood 1990 76:1110.

Broxmeyer et al., "Myelopoietic enhancing effects of murine macrophage inflammatory proteins and human bone marrow granulocyte/macrophage progenitor cells", J. Exp. Med. 1989 170:1583.

Broxmeyer et al., "The production of myeloid good cells and their regulation during health and disease", CRC Crit. Rev. Oncol./Ilematol. 1988 8:173.

Broxmeyer et al., "Macrophage inflammatory protein (MIP)—1β subrogates the capacity of MIP-1α to suppress myeloid progenitor cell growth", 1991 147:2586.

Carthew et al., Cell 1990 63:561-577.

Cohen et al., "Mounting a Targeted Strike on Unwanted Immune Responses", Science 1992 257:751.

Davatelis et al., "Macrophage inflammatory protein-1:a ostaglandin-independent endogenous pyrogen", Science 1989 243:1066.

Davatelis et al., "Cloning and Characterization of a cDNA for murine macrophage inflammatory protein (MIP), a cell monokine with inflammatory and chemokinetic properties", J. Experimental Medicine, 1988 167:1939.

Debenedette et al., J. Immunol. 1997 158:551-559.

DeBenedette et al., "Role of 4-1BB Ligand in Constimulation of T Lymphocyte Growth and its Upregulation on M12 B Lymphomas by cAMP", J. Exp. Med. 1995 181:8.

Defrance et al., J. Exp. Med. 1992 175:671-682.

Dunlop et al., "Demonstration of Stem Cell Inhibition and Myeloproteactive Effects of SCI/rhMIP1α in Vivo", Blood 1992 79:2221-2225.

Fahey et al., "Cytokine induction in a model of wound healing:the appearance of MIP-1, MIP-2, hectin/TNF and IL-I", Cytokine 1990 2(2):92-99.

Gimmi et al., "Human T-cell clonal anergy is induced by antigen presentation in the absence of B7 costimulation", Proc. Natl. Acad. Sci. 1993 90:6586-6590.

Goodwin et al., "Molecular cloning of a ligand for the inducible T cell gene 4-1BB:a member of an emerging family of sytokines with homology to tumor necrosis factor", Eur. J. Immunol. 1993 23:2631-2641.

Graham et al., "Identification and characterization of an inhibitor of hemopoietic stem cells proliferation", Nature 1990 144:442.

Haskins et al., J. Exp. Med. 1993 157:1149-1169.

Hong et al., J. Immunother. 2000 23:613.

Kwon et al., Cell Immunol. 1989 121:414-422.

Kwon et al., J. Virology 1984 52:1000-1004.

Kwon et al., Biochem. & Biophys. Res. Comm. 1989 158:1-10.

Kwon et al., "Isolation and initial characterization of multiple species of T-lymphocyte subset cDNA clones", Proc. Natl. Acad. Sci. USA 1987 84:2896.

Kim et al., "Novel T Cell Antigen 4-1BB Associates with the Protein Tyrosine Kinase $p56^{lck1}$", J. Immunology 1993 151:1255-1263.

Lenschow et al., "Long-Term Survival of Xeogeneic Pancreatic Islet Grafts Induced by CTLA41g", 1992 Science 275:789-792.

Lewin et al., "When does Homology Mean Something Else?", Science 1987 237:1570.

Maniatis et al., Molecular Cloning:A Laboratory Manual (Cold Spring Harbor Laboratory, Cold Spring Harbor, NY 1982 310-352.

Maraskovsky et al., Inernat. Immunol. 1992 4:475-485.

Miller et al., "A level polypeptide secreted by activated human T lymphocytes", J. Immunol. 1989 3:2907.

Minano et al., "Macrophage inflammatory protein-1:unique action on the hypothalamus to evoke fever", Brain Bull. 1990 24:849-852.

Mittler et al., J. Exp. Med. 1999 10:1535.

Mueller et al., Ann. Rev. Immunol. 1989 7:445-480.

Noelle et al., Immunol. Today 1990 11:361-368.

Obaru et al., "A cDNA clone used study mRNA induction in human tonsillar lymphocytes by a tumor promoter", Biochem. 1986 99:885.

Oh et al., "Identification of cell surface receptors of murine macrophage inflammatory protein-1α", J. Immunol. 1991 147:2978-2983.

Oppenheim et al., "Properties of the novel proinflammatory supergene "intercrine" cytokine family", Ann. Rev. Immunol. 1991 9:617.

Petchen-Matthews, "Differential Endocytosis of CD4 in Lymphocytic and Nonlymphocytic Cells", J. Exp. Med. 1991 173:575-587.

Reeck et al., "Homology in Proteins and Nucleic Acids:A Terminology Muddle and a Way out of It", Cell 1987 50:667.

Schall et al., "A Human T-Cell Specific Molecule is a Member of a New Gene Family", J. Immunol. 1988 141:1018-1025.

Schwarz et al., "ILA, the Human 4-IBB Homologue, Is Inducible in Lymphoid and Other Cell Lineages", Blood 1995 85:1043-1052.

Sherry et al., "Resolution of the two components of macrophage inflammatory protein 1, and cloning and characterization of one of those components, macrophage inflammatory protein 1β", J. Experimental Medicine 1988 168:2251.

Shuford et al., J. Exp. Med. 1997 186 7-55.

Suggs et al., "Use of synthetic oligonucleotides as hybridization probes:Isolation of cloned cDNA sequences for human $B_2$-microglobulin", Proc. Natl. Acad. USA 78:6613-6617, 1981.

Tekamp-Olson et al., "Cloning and characterization of mRNAs for murine macrophage inflammatory protein 2 and its human homologues", J. Exp. Med. 1990 172:911.

Turka et al., Proc. Natl. Acad. Sci. USA 1992 89:11102-11105.

Van Lier et al., J. Immunol. 139:1589-1596, 1987.

Wolpe et al., "Macrophage inflammatory proteins 12:members of a novel superfamily of cytokines", FASEB 1989 3:2565.

Wolpe et al., "Macrophages secrete a novel heparin-binding protein with inflammatory and rophil chemokinetic properties", J. Exp. Med. 1988 167:570.

Wolpe et al., "Identification and characterization of macrophage inflammatory protein 2", Proc. Natl. Acad. Sci. USA 1989 86:612.

Zipfel et al., "Mitogenic activation of human T cells induces two closely related genes which share structural similarities with a new family of secreted factors", J. Immunol. 1989 142:1582.

Callard et al., "The Cytokine FactsBook", Academic Press: London 1994 39-40.

Lerner R.A., "Antibodies of Predetermined specificity in Biology and Medicine", Adv. Immunol. 1984 36:1-44.

* cited by examiner

```
ATGTCCATGA ACTGCTGAGT GGATAAACAG CACGGGATAT CTCTGTCTAA        -96
AGGAATATTA CTACACCAGG AAAAGGACAC ATTCGACAAC AGGAAAGGAG        -46
CCTGTCACAG AAAACCACAG TGTCCTGTGC ATGTGACATT TCGCC             -1
```

| | | | | | | | | | | | | | | | |
|---|---|---|---|---|---|---|---|---|---|---|---|---|---|---|---|
| ATG | GGA | AAC | AAC | TGT | TAC | AAC | GTG | GTG | GTC | ATT | GTG | CTG | CTG | CTA | 45 |
| Met | Gly | Asn | Asn | Cys | Tyr | Asn | Val | Val | Val | Ile | Val | Leu | Leu | Leu | |
| GTG | GGC | TGT | GAG | AAG | GTG | GGA | GCC | GTG | CAG | AAC | TCC | TGT | GAT | AAC | 90 |
| Val | Gly | Cys | Glu | Lys | Val | Gly | Ala | Val | Gln | Asn | Ser | Cys | Asp | Asn | |
| TGT | CAG | CCT | GGT | ACT | TTC | TGC | AGA | AAA | TAC | AAT | CCA | GTC | TGC | AAG | 135 |
| Cys | Gln | Pro | Gly | Thr | Phe | Cys | Arg | Lys | Tyr | Asn | Pro | Val | Cys | Lys | |

H4-1BB FI →

| | | | | | | | | | | | | | | | |
|---|---|---|---|---|---|---|---|---|---|---|---|---|---|---|---|
| AGC | TGC | CCT | CCA | AGT | ACC | TTC | TCC | AGC | ATA | GGT | GGA | CAG | CCG | AAC | 180 |
| Ser | Cys | Pro | Pro | Ser | Thr | Phe | Ser | Ser | Ile | Gly | Gly | Gln | Pro | Asn | |

H4-1BB FII →

| | | | | | | | | | | | | | | | |
|---|---|---|---|---|---|---|---|---|---|---|---|---|---|---|---|
| TGT | AAC | ATC | TGC | AGA | GTG | TGT | GCA | GGC | TAT | TTC | AGG | TTC | AAG | AAG | 225 |
| Cys | Asn | Ile | Cys | Arg | Val | Cys | Ala | Gly | Tyr | Phe | Arg | Phe | Lys | Lys | |
| TTT | TGC | TCC | TCT | ACC | CAC | AAC | GCG | GAG | TGT | GAG | TGC | ATT | GAA | GGA | 270 |
| Phe | Cys | Ser | Ser | Thr | His | Asn | Ala | Glu | Cys | Glu | Cys | Ile | Glu | Gly | |
| TTC | CAT | TGC | TTG | GGG | CCA | CAG | TGC | ACC | AGA | TGT | GAA | AAG | GAC | TGC | 315 |
| Phe | His | Cys | Leu | Gly | Pro | Gln | Cys | Thr | Arg | Cys | Glu | Lys | Asp | Cys | |
| AGG | CCT | GGC | CAG | GAG | CTA | ACG | AAG | CAG | GGT | TGC | AAA | ACC | TGT | AGC | 360 |
| Arg | Pro | Gly | Gln | Glu | Leu | Thr | Lys | Gln | Gly | Cys | Lys | Thr | Cys | Ser | |

← H4-1BB RI

| | | | | | | | | | | | | | | | |
|---|---|---|---|---|---|---|---|---|---|---|---|---|---|---|---|
| TTG | GGA | ACA | TTT | AAT | GAC | CAG | AAC | GGT | ACT | GGC | GTC | TGT | CGA | CCC | 405 |
| Leu | Gly | Thr | Phe | Asn | Asp | Gln | Asn | Gly | Thr | Gly | Val | Cys | Arg | Pro | |

← H4-1BB RII

| | | | | | | | | | | | | | | | |
|---|---|---|---|---|---|---|---|---|---|---|---|---|---|---|---|
| TGG | ACG | AAC | TGC | TCT | CTA | GAC | GGA | AGG | TCT | GTG | CTT | AAG | ACC | GGG | 450 |
| Trp | Thr | Asn | Cys | Ser | Leu | Asp | Gly | Arg | Ser | Val | Leu | Lys | Thr | Gly | |
| ACC | ACG | GAG | AAG | GAC | GTG | GTG | TGT | GGA | CCC | CCT | GTG | GTG | AGC | TTC | 495 |
| Thr | Thr | Glu | Lys | Asp | Val | Val | Cys | Gly | Pro | Pro | Val | Val | Ser | Phe | |
| TCT | CCC | AGT | ACC | ACC | ATT | TCT | GTG | ACT | CCA | GAG | GGA | GGA | CCA | GGA | 540 |
| Ser | Pro | Ser | Thr | Thr | Ile | Ser | Val | Thr | Pro | Glu | Gly | Gly | Pro | Gly | |
| GGG | CAC | TCC | TTG | CAG | GTC | CTT | ACC | TTG | TTC | CTG | GCG | CTG | ACA | TCG | 585 |
| Gly | His | Ser | Leu | Gln | Val | Leu | Thr | Leu | Phe | Leu | Ala | Leu | Thr | Ser | |
| GCT | TTG | CTG | CTG | GCC | CTG | ATC | TTC | ATT | ACT | CTC | CTG | TTC | TCT | GTG | 630 |
| Ala | Leu | Leu | Leu | Ala | Leu | Ile | Phe | Ile | Thr | Leu | Leu | Phe | Ser | Val | |

*Fig. 1A*

```
CTC AAA TGG ATC AGG AAA AAA TTC CCC CAC ATA TTC AAG CAA CCA      675
Leu Lys Trp Ile Arg Lys Lys Phe Pro His Ile Phe Lys Gln Pro

TTT AAG AAG ACC ACT GGA GCA GCT CAA GAG GAA GAT GCT TGT AGC      720
Phe Lys Lys Thr Thr Gly Ala Ala Gln Glu Glu Asp Ala Cys Ser

TGC CGA TGT CCA CAG GAA GAA GAA GGA GGA GGA GGA GGC TAT GAG      765
Cys Arg Cys Pro Gln Glu Glu Glu Gly Gly Gly Gly Gly Tyr Glu

CTG TGA                                                          771
Leu ---

TGTACTATCC  TAGGAGATGT  GTGGGCCGAA  ACCGAGAAGC  ACTAGGACCC       821
CACCATCCTG  TGGAACAGCA  CAAGCAACCC  CACCACCCTG  TTCTTACACA       871
TCATCCTAGA  TGATGTGTGG  GCGCGCACCT  CATCCAAGTC  TCTTCTAACG       921
CTAACATATT  TGTCTTTACC  TTTTTTAAAT  CTTTTTTTAA  ATTTAAATTT       971
TATGTGTGTG  AGTGTTTTGC  CTGCCTGTAT  GCACACGTGT  GTGTGTGTGT      1021
GTGTGTGACA  CTCCTGATGC  CTGAGGAGGT  CAGAAGACAA  AGGGTTGGTT      1071
CCATAAGAAC  TGGAGTTATG  GATGGCTGTG  AGCCGGNNNG  ATAGGTCGGG      1121
ACGGAGACCT  GTCTTCTTAT  TTTAACGTGA  CTGTATAATA  AAAAAAAAAT      1171
GATATTTCGG  GAATTGTAGA  GATTGTCCTG  ACACCCTTCT  AGTTAATGAT      1221
CTAAGAGGAA  TTGTTGATAC  GTAGTATACT  GTATATGTGT  ATGTATATGT      1271
ATATGTATAT  ATAAGACTCT  TTTACTGTCA  AAGTCAACCT  AGAGTGTCTG      1321
GTTACCAGGT  CAATTTTATT  GGACATTTTA  CGTCACACAC  ACACACACAC      1371
ACACACACAC  ACGTTTATAC  TACGTACTGT  TATCGGTATT  CTACGTCATA      1421
TAATGGGATA  GGGTAAAAGG  AAACCAAAGA  GTGAGTGATA  TTATTGTGGA      1471
GGTGACAGAC  TACCCCTTCT  GGGTACGTAG  GGACAGACCT  CCTTCGGACT      1521
GTCTAAAACT  CCCCTTAGAA  GTCTCGTCAA  GTTCCGGAC   GAAGAGGACA      1571
GAGGAGACAC  AGTCCGAAAA  GTTATTTTTC  CGGCAAATCC  TTTCCCTGTT      1621
TCGTGACACT  CCACCCCTTG  TGGACACTTG  AGTGTCATCC  TTGCGCCGGA      1671
AGGTCAGGTG  GTACCGTCT   GTAGGGCGG   GGAGACAGAG  CCGCGGGGA       1721
GCTACGAGAA  TCGACTCACA  GGGCGCCCCG  GCTTCGCAA   ATGAAACTTT      1771
TTTAATCTCA  CAAGTTTCGT  CCGGGCTCGG  CGGACCTATG  GCGTCGATCC      1821
TTATTACCTT  ATCCTGGCGC  CAAGATAAAA  CAACCAAAAG  CCTTGACTCC      1871
GGTACTAATT  CTCCCTGCCG  GCCCCGTAA   GCATAACGCG  GCGATCTCCA      1921
CTTTAAGAAC  CTGGCCGCGT  TCTGCCTGGT  CTCGCTTTCG  TAAACGGTTC      1971
TTACAAAAGT  AATTAGTTCT  TGCTTTCAGC  CTCCAAGCTT  CTGCTAGTCT      2021
ATGGCAGCAT  CAAGGCTGGT  ATTTGCTACG  GCTGACCGCT  ACGCCGCCGC      2071
AATAAGGGTA  CTGGGCGGCC  CGTCGAAGGC  CCTTTGGTTT  CAGAAACCCA      2121
AGGCCCCCCT  CATACCAACG  TTTCGACTTT  GATTCTTGCC  GGTACGTGGT      2171
GGTGGGTGCC  TTAGCTCTTT  CTCGATAGTT  AGAC                        2205
```

Fig. 1B human homologue of mouse 4-1bb h4-1bb   Length 838

```
  1  AATCAGCTTT GCTAGTATCA TACCTGTGCC AGATTTCATC ATGGGAAACA
 51  GCTGTTACAA CATAGTAGCC ACTCTGTTGC TGGTCCTCAA CTTTGAGAGG
101  ACAAGATCAT TGCAGGATCC TTGTAGTAAC TGCCCAGCTG GTACATTCTG
151  TGATAATAAC AGGAATCAGA TTTGCAGTCC CTGTCCTCCA AATAGTTTCT
201  CCAGCGCAGG TGGACAAAGG ACCTGTGACA TATGCAGGCA GTGTAAAGGT
251  GTTTTCAGGA CCAGGAAGGA GTGTTCCTCC ACCAGCAATG CAGAGTGTGA
301  CTGCACTCCA GGGTTTCACT GCCTGGGGGC AGGATGCAGC ATGTGTGAAC
351  AGGATTGTAA ACAAGGTCAA GAACTGACAA AAAAAGGTTG TAAAGACTGT
401  TGCTTTGGGA CATTTAACGA TCAGAAACGT GGCATCTGTC GACCCTGGAC
451  AAACTGTTCT TTGGATGGAA AGTCTGTGCT TGTGAATGGG ACGAAGGAGA
501  GGGACGTGGT CTGTGGACCA TCTCCAGCTG ACCTCTCTCC GGGAGCATCC
551  TCTGTGACCC CGCCTGCCCC TGCGAGAGAG CCAGGACACT CTCCGCAGAT
601  CATCTCCTTC TTTCTTGCGC TGACGTCGAC TGCGTTGCTC TTCCTGCTGT
651  TCTTCCTCAC GCTCCGTTTC TCTGTTGTTA AACGGGGCAG AAAGAAACTC
701  CTGTATATAT TCAAACAACC ATTTATGAGA CCAGTACAAA CTACTCAAGA
751  GGAAGATGGC TGTAGCTGCC GATTTCCAGA AGAAGAAGAA GGAGGATGTG
801  AACTGTGAAA TGGAAGTCAA TAGGGCTGTT GGGACTTT
```

Fig. 2A

```
  1  MGNSCYNIVA TLLLVLNFER TRSLQDPCSN CPAGTFCDNN RNQICSPCPP
 51  NSFSSAGGQR TCDICRQCKG VFRTRKECSS TSNAECDCTP GFHCLGAGCS
101  MCEQDCKQGQ ELTKKGCKDC CFGTFNDQKR GICRPWTNCS LDGKSVLVNG
151  TKERDVVCGP SPADLSPGAS SVTPPAPARE PGHSPQIISF FLALTSTALL
201  FLLFFLTLRF SVVKRGRKKL LYIFKQPFMR PVQTTQEEDG CSCRFPEEEE
251  GGCEL
```

Fig. 2B

COGNITIVE PHASE
EARLY ACTIVATION

PROLIFERATION
CLONAL EXPANSION
LATE ACTIVATION

BLOCKING STEPS IN T-CELL ACTIVATION PATHWAY

NUCLEIC ACID MOLECULES ENCODING HUMAN 4-1BB

This application is a continuation of U.S. application Ser. No. 08/955,572, filed Oct. 22, 1997, now abandoned, which is a file wrapper continuation of U.S. application Ser. No. 08/461,652, filed Jun. 5, 1995 now abandoned, which is a division of U.S. application Ser. No. 08/122,796, filed Sep. 16, 1993, abandoned.

Part of the work during the development of this invention was made with government support from the National Institutes of Health under grant numbers IR23A123058, R01 A128175 and P60 KD20542. The U.S. Government has certain rights in the invention.

FIELD OF THE PRESENT INVENTION

The present invention relates to a previously unknown human receptor protein, H4-1BB, which was isolated and identified based upon work with a homologous murine (mouse) receptor protein, 4-1BB, which was isolated and identified by specific expression of the T cell genes by the present inventor.

BACKGROUND OF THE PRESENT INVENTION

The immune system of humans and other species requires that white blood cells be made in the bone marrow, which white blood cells include phagocytes, lymphocytes and B cells. As presently understood, the phagocytes include macrophage cells which scavenge unwanted materials such as virus protein from the system. The lymphocytes include helper T cells and killer T cells and B cells as well as other cells, including those categorized as suppressor T cells. The B cells produce the antibodies. The killer T cells physically pierce the cell and the helper T cells facilitate the whole process. In any event, the immune process is facilitated by lymphokines.

Lymphokines are the proteins by which the immune cells communicate with each other. Scientists produce them in sufficient quantities for therapeutic use against immunologic diseases. There are many known lymphokine proteins and they include the interferons, interleukin-1,2,3,4,5,6,7, colony-stimulating factors, lymphotoxin, tumor necrosis factor and erythropoietin, as well as others.

Interleukin 1, secreted from macrophages activate the helper T cells and raise the body temperature causing fever which enhances the activity of the immune cells. The activated helper T Cells produce Interleukin 2 and Interleukin 2 stimulates the helper and killer T cells to grow and divide. The helper T cells also produce another lymphokine, B cell growth factor (BCGF), which causes B cells to multiply. As the number of B cells increases, the helper T cells produce another lymphokine known as the B cell differentiating factor (BCDF), which instructs some of the B cells to stop replicating and start producing antibodies. T cells also produce a lymphokine, gamma interferon (IF), which has multiple effects like Interleukin 2. Interferon helps activate killer T cells, enabling them to attack the invading organisms. Like BCGF, interferon increases the ability of the B cells to produce antibodies. Interferon also affects the macrophages to keep them at the site of the infection and help the macrophages to digest the cells they have engulfed. Gathering momentum with each kind of lymphokine signal between the macrophages and the T cells, the lymphokines amplify the immune system response and the virus protein or other foreign matter on the infected cells is overwhelmed. There are many other lymphokines, maybe a hundred or more, which participate in the immune process. Many lymphokines are known and many are not.

Lymphokines are sometimes called intercellular peptide signals. Among scientists there is widespread use of cloned cell lines as lymphokine producers and the isolation of lymphokine mRNA has become a common technique. The mouse receptor protein, 4-1BB, was isolated and identified based on specific expression of the T cell genes using a technique identified by the present inventor in a publication (Proc. Natl. Acad. Sci. USA. 84, 2896-2900, May 1987, Immunology). The protocol reported in this publication can be used by scientists to detect virtually all of the lymphokines. The method is designed to detect virtually all mRNA expressed differentially and the mRNA sequences of the immune cells are expressed differentially (as they relate to the T cells and the killer T cells) even though the level of expression is low and the quantity of the secreted lymphokine protein is low. The present inventor believes that the analysis described in the above identified publication can reveal biologically important molecules such as lymphokines because there are many indications that biologically important or active molecules are coded by the most scarce messages. An example is a transforming growth factor (TGF) which is present as only one of a million clones.

Most T cell factors have been classically identified by recognizing biologic activities in assays, purifying the protein information. An alternative approach is to isolate putative T cell genes based upon specific expression and then demonstrate the function of the unknown molecule. Using the aforesaid modified differential screening procedure, the present inventor cloned a series of T cell subset-specific cDNAs from cloned helper T (HTL) L2 and cloned cytolytic T lymphocyte (CTL) L3.

A series of T-cell subset-specific cDNAs were isolated from cloned murine T-cells by employing a modified differential screening procedure. The nucleotide sequence and expression properties of some of the cDNA species have been reported. One of the genes not previously characterized, that encodes mouse receptor protein 4-1BB, was studied further. These studies have led to the isolation of the human homologue to 4-1BB, H4-1BB.

SUMMARY OF THE PRESENT INVENTION

The present invention includes the human receptor protein H4-1BB and the cDNA gene encoding for human receptor protein H4-1BB. The nucleotide sequence of the isolated cDNA is disclosed herein along with the deduced amino acid sequence. The cDNA gene identified as pH4-1BB was deposited at the Agricultural Research Service Culture Collection and assigned the accession number: NRRL B21131.

The cDNA, and fragments and derivatives thereof, can be used as a probe to isolate DNA sequences encoding for proteins similar to the receptor protein encoded by the cDNA. The cDNA of the human receptor H4-1BB is about 65% homologous to the mouse cDNA 4-1BB and was isolated by using probes derived from cDNA 4-1BB. The cDNA gene identified as p4-1BB was deposited at the American Type Culture Collection at 12301 Parklawn Drive, Rockville, Md. 20852 under ATCC No.: 67825.

The human receptor protein H4-1BB can be produced by: 1) inserting the cDNA of H4-1BB into an appropriate expression vector, 2) transfecting the expression vector into an appropriate transfection host, c) growing the transfected hosts in appropriate culture media and d) purifying the receptor protein from the culture media. The protein and fragments and derivatives can be used: 1) as a probe to isolate ligands to human receptor protein H4-1BB, 2) to stimulate proliferation of B-cells expressing 4-1BB ligands, or 3) to block H4-1BB ligand binding.

B-cell proliferation can be induced by treating B-cells that have expressed a ligand to receptor protein H4-1BB with cells that have expressed receptor protein H4-1BB. The use of H4-1BB to block H4-1BB ligand binding has practical application in the suppression of the immune system during organ transplantation. A similar costimulatory immune system pathway is being analyzed for this type of application. See "Mounting a Targeted Strike on Unwanted Immune Responses", Jon Cohen, Science, Vol. 257, 8-7-92; "Long Term Survival of Xenogeneic Pancreatic Islet Grafts Induced by CTLA4Ig", Lenschow et al, Science Vol. 257, 7-8-92; and "Immunosuppression in Vivo by a Soluble Form of the CTLA-4 T Cell Activation Molecule", Linsley et al, Science Vol. 257 7-8-92.

A monoclonal antibody against H4-1BB can be used to enhance T-cell proliferation by treating T-cells that have expressed receptor protein H4-1BB with the anti H4-1BB monoclonal antibody. Some tumors are potentially immunogenic but do not stimulate an effective anti-immune response in vivo. Tumors may be capable of delivering antigen-specific signals to T cells, but may not deliver the co-stimulatory signals necessary for full activation of T cells. Expression of the co-stimulatory ligand B7 on of melanoma cells was found to induce the rejection of a murine melanoma in vivo. ("Tumor Rejection After Direct Co-Stimulation of $CD8^+$ T Cells by B7-Transfected Melanoma Cells", Sarah E. Townsend and James P. Allison, Science Vol. 259, 1-5-93.) A monoclonal antibody against H4-1BB may be capable of the same effect as it is now known to induce T cell proliferation and activation.

A fusion protein for detecting cell membrane ligands to human receptor protein H4-1BB was developed. It comprises the extracellular portion of the receptor protein H4-1BB and a detection protein (alkaline phosphatase) bound to the portion of the receptor protein H4-1BB. The portion of the receptor protein H4-1BB binds to the cell membrane ligands and binding can be detected by relative activity assays for the detection protein. The fusion protein is placed in the presence of a cell suspected to express the receptor protein H4-1BB. Then the cell is washed of any fusion protein not bound to the cell membrane ligands. Once the washed cells are placed in the presence of a substrate for the detection protein and the relative activity of the detection protein can be measured.

The primary object of the present invention is the identification of the new human receptor, H4-1BB as identified herein by its sequence.

Another object of the present invention is to teach a fusion protein comprising the extracellular portion of H4-1BB and a detection protein.

Still another object of the present invention is to teach methods of using the cDNA H4-1BB, the receptor protein H4-1BB, the monoclonal antibody and the ligand for H4-1BB.

BRIEF DESCRIPTIONS OF THE FIGURES

FIGS. 1a and 1b show the sequence for the cDNA of mouse receptor protein 4-1BB and the regions used as PCR primers to obtain the human homologue H4-1BB.

FIGS. 2a and 2b show the nucleotide sequence and the deduced amino acid sequence of human receptor H4-1BB respectively.

Figure 4A:
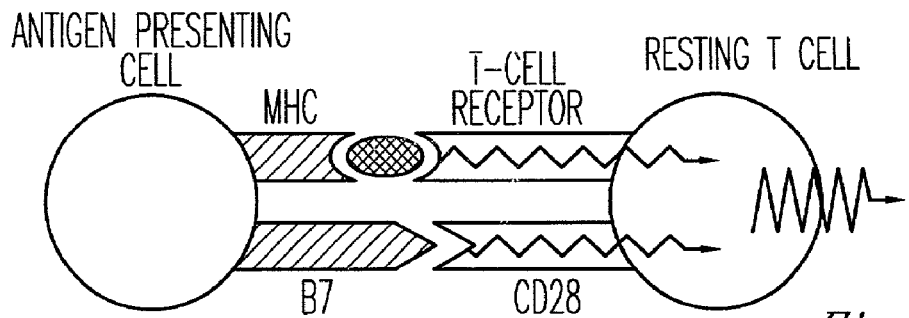
Figure 4B:
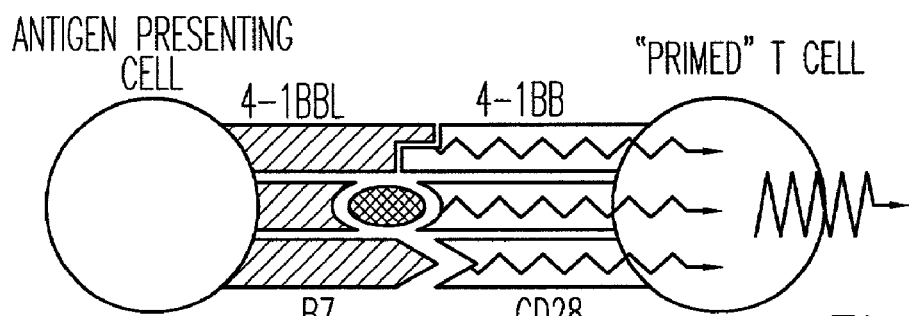
Figure 4C:
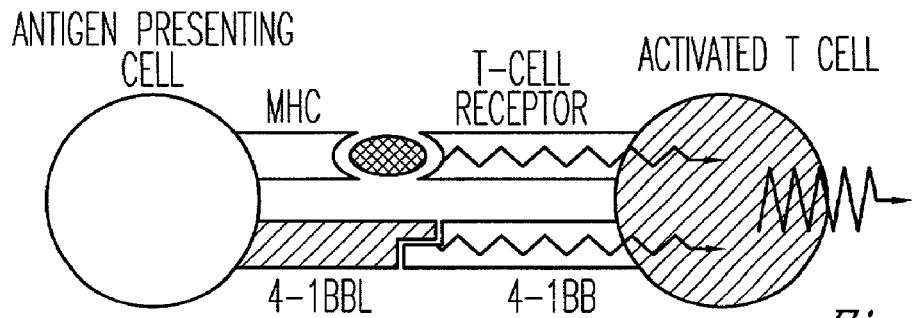

FIGS. 4a, 4b, and 4c illustrate a normal T-cell activation pathway.

Figure 5A:
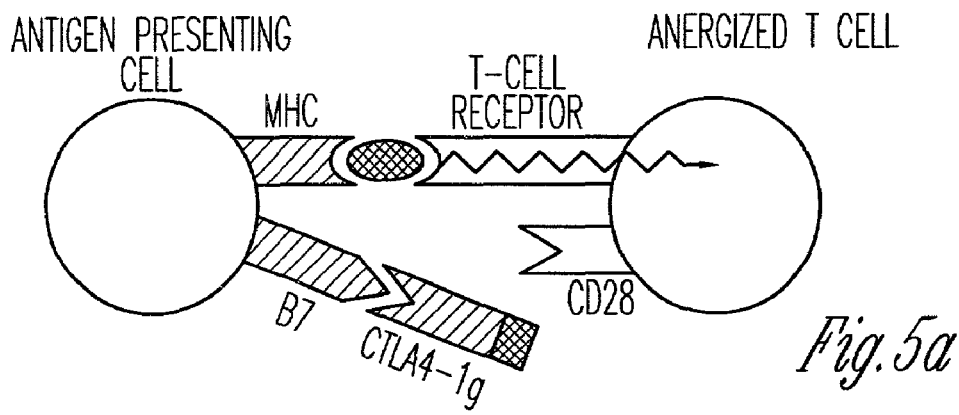
Figure 5B:
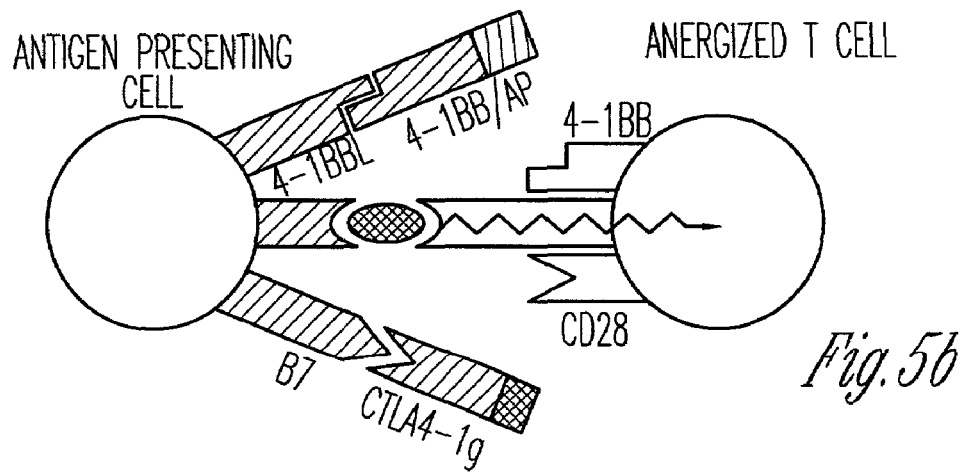
Figure 5C:
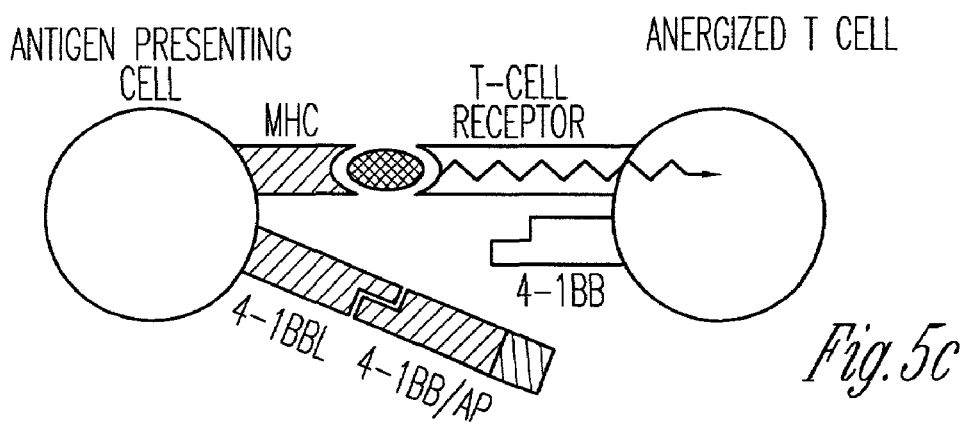

FIGS. 5a, 5b, and 5c illustrate CTLA4-lg alone, 4-1BB/AP and CTLA4-lg together and 4-1BB/AP alone respectively being used to block steps in the T-cell activation pathway.

DETAILED DESCRIPTION

In the following detailed description references are made to known procedures and studies, as well as published work of the applicant. These publications are incorporated herein by reference for clarity and listed in an appendix included at the end of this detailed description.

Isolation and Characterization of Mouse Receptor 4-1BB

FIGS. 1a and 1b show the nucleotide sequence and the deduced amino acid sequence of the mouse receptor 4-1BB. The nucleotides of the message strand are numbered in the 5' to 3' direction and numbers are shown on both sides of the sequence. Nucleotide residue 1 is the A of the initiation codon ATG, and the nucleotides on the 5' side of residue 1 are indicated by negative numbers. The predicted amino acid sequence is shown below the nucleotide sequence. Putative signal peptide is underlined. Stop codon is indicated by ( - - - ). Cysteine residues are highlighted by the dots. An unusual feature of 4-1BB sequence is that there is a potential polyadenylation signal of AATAAA at nucleotides 1158-1163 (FIG. 1b boxed). It was believed that this signal was functional because this gene produces at least two different sizes of mRNA.

The transcript of 4-1BB was inducible by concanavalin A in mouse splenocytes, T-cell clones, and hybridomas. The expression of 4-1BB transcripts was inhibited by cyclosporin A. The 4-1BB mRNA was inducible by antigen receptor stimulation but was not inducible by Il-2 stimulation in the cloned T-cells (1). The 4-1BB cDNA encodes a peptide of 256 amino acids containing a putative leader sequence, a potential membrane anchor segment, and other features of known receptor proteins. Therefore, the expression pattern of 4-1BB resembles those of lymphokine mRNAs while the sequence appeared consistent with those of receptor proteins.

The major species of 4-1BB on the cell surface appears to be a 55-kDa dimer. 4-1BB also appears to exist as a 30-kDa monomer and possibly as a 110-kDa tetramer. Since these 4-1BB species were immunoprecipitated from a homogenous population of cells (T cell clone F1), all forms potentially co-exist on each cell. A comparison of peptide digests from the 4-1BB monomer and dimer will be needed to determine whether 4-1BB exists as a homodimer on the cell surface. A variety of cell surface receptors such as the insulin receptor (2), the B cell surface immunoglobulin receptor (3), the T cell Ag receptor (4), the CD28 costimulatory receptor (5), and the CD27 T cell antigen (6) are composed of disulfide-bonded subunits. Receptor dimerization may be required for ligand binding and subsequent biochemical signaling.

4-1BB is not expressed on resting T cells but is inducible by activators which deliver a complete growth stimulus to the T cell. The combination of PMA and ionomycin is capable of mimicking those signals required for T cell proliferation. Although PMA or ionomycin alone induced 4-1BB mRNA, the combination of PMA and ionomycin resulted in optimal 4-1BB expression. Furthermore, the expression of 4-1BB was not transient. When purified splenic T cells were stimulated with immobilized anti-CD3, 4-1BB mRNA was expressed and this expression was maintained for up to 96 hrs poststimulation. Cell cycle analysis will be required to confirm that 4-1BB is expressed throughout cell cycle progression.

4-1BB is structurally related to members of the nerve growth factor receptor super-family. Although these receptors possess structurally similar ligand-binding properties (cysteine-rich regions), the cytoplasmic domains of these proteins are nonconserved which could allow for diversity in transmembrane signaling. Some members of this family are involved in the T or B cell activation process. There are in vitro functional data on the OX-40, CD40 and CD27 antigens. Antibodies against the OX-40 augment the T cell response in a mixed lymphocyte reaction (7) and antibodies against CD40 enhance B-cell proliferation in the presence of a coactivator, such as PMA or CD20 antibodies, and synergize with IL-4 in vitro to induce B-cell differentiation and to generate long-term normal B cell lines (8). One monoclonal antibody, anti-1A4, which recognizes an epitope on the CD27 molecule inhibited calcium mobilization, IL-2 secretion, helper T cell function, and T cell proliferation. On the other hand, CLB-CD27/1, another anti-CD27 mAb enhanced proliferation of human T cells stimulated with PHA or anti-CD3 mAb (6). These results indicate that the CD27 molecule plays an important role in T cell activation. Except for TNFRs, NCFR and CD40, the ligands or cell surface molecules to which the members of the superfamily bind are not yet identified. Identification and characterization of the ligands to which the receptors bind will be helpful in better defining the physiologic role of 4-1BB.

To ascertain whether cell surface 4-1BB could contribute to T cell activation, the anti-4-1BB 53A2 was used as an antagonist to 4-1BB. These data suggested that 4-1BB does in fact have the potential to function as an accessory signaling molecule during T cell activation and proliferation. The addition of soluble 53A2 to purified splenic T cells stimulated with immobilized anti-CD3 resulted in an amplification of $^3$H thymidine incorporation compared to T cells stimulated with anti-CD3 alone. This pattern of enhancement ranged from 2- to 10-fold in three independent experiments.

In the original two signal model of Bretcher and Cohn, they proposed that signal 1, the occupancy of the T cell antigen receptor (TCR), resulted in inactivation of the T cell in the absence of signal 2, which is provided by accessory cells. This has since been confirmed by a variety of studies (9). The identification of the accessory cell CD28 as a potent costimulatory receptor on T cells was a significant contribution in beginning to characterize the accessory signal(s) required for optimal T cell proliferation (10). It is possible that other cell surface molecules may contribute to these costimulatory activation requirements (11).

The biochemical signals delivered through 4-1BB are not completely known. One possibility considered was the observation that 4-1BB contains a putative $p56^{kk}$ tyrosine kinase binding domain in its cytoplasmic tail. It was later determined that $p56^{kk}$ tyrosinase kinase binds to 4-1BB. It will also be worthwhile to determine if 4-1BB-mediated signaling can regulate genes such as IL-2 and IL-2 receptor, whose expression is required for T cell activation and subsequent proliferation.

Although the precise functions of members of the Nerve Growth Factor Receptor (NGFR) family appear to be diverse, an emerging theme is one in which these molecules may contribute in various ways to a maintenance of responsiveness or viability of the particular cell type in which they are expressed. For instance, NGF is absolutely required for viability of neurons in vitro and in vivo (12). The crosslinking of CD40 by soluble antiCD40 monoclonal antibody blocks germinal center centrocytes from undergoing apoptosis in vitro (13). Signals delivered through CD40 may also aid in maintenance of responsiveness to differentiation factors. The ligation of CD40 with anti-CD40 F(ab')$_2$ fragments in the presence of IL-4 induced large increases IgE synthesis (14). Also, anti-CD40 activated naive B cells treated with IL-10 and transforming growth factor-β became committed to IgA secretion (15).

In addition to sharing the molecular characteristics with the NGFR superfamily, it was noted that the 4-1BB contained a putative zinc finger structure of the yeast elF-2β protein (16). 4-1BB also shares a conserved region with the sina seven in absentia of *Drosophila*, which is required for correct photoreceptor cell development (17). That particular region is also similar to the protein product of the DG17 gene of *Dictyostelium*, whose expression is specifically induced during aggregation by cAMP (18).

This region forms the pattern of $C-X_2-C-X_9-C-X_3-H-X_3-C-X-C$; and the cysteines and histidine are conserved in a similar space in 4-1BB, sina, and DG17 proteins. Ten of 24 amino acids between the 4-1BB and sina proteins are identical, and 3 of 24, are conservative substitutes. The conserved pattern suggests that these amino acids are functionally important. The sina protein is localized in the nucleus, suggesting that it has a regulatory function in cells. The fact that the amino acid sequence of 4-1BB contains features like a zinc finger motif, a nuclear protein, and a receptor domain suggests that 4-1BB may play diverse roles during cellular proliferation and differentiation.

4-1BB may represent another cell-surface molecule involved in T cell-APC interactions. The 4-1BB-AP fusion protein specifically bound to mature B-cell lines, anti-μ-activated primary B cells, and mature macrophage-cell lines. 4-1BB-AP bound at low or insignificant levels to immature B- and macrophage-cell lines, T-cell clones, T-cell lines, primary culture T cells, and various nonlymphoid-cell lines. Since 4-1BB-AP binds to mature B cells and macrophages, it is possible that signals delivered upon 4-1BB binding may modulate APC functions in some way. This possibility remains to be explored.

Chalupny and colleagues (19) have proposed that 4-1BB Rg, a fusion protein consisting of the extracellular domain of 4-1BB and the Fc region of human IgG, bound to the extracellular matrix (ECM). The highest level of 4-1BB Rg binding was to human vitronectin. In data not shown, an ELISA was performed using 4-1BB-AP and human vitronectin (Yelios Pharmaceuticals/GIBCO-BRL, Grand Island, N.Y.) immobilized at 0.007 μg-10 μg per well on microtiter plates. No binding of 4-1BB-AP based on AP activity was observed. To rule out the possibility that 4-1BB-AP was binding to proteins extrinsically attached to the cell surface (possible extracellular matrix components), B-cell lymphomas were washed in acid conditions prior to the binding assay. 4-1BB-AP still bound specifically to mature B-cell lymphomas. It is still to be determined whether a 4-1BB-ligand specifically expressed on B cells and macrophages exists, and whether 4-1BB-AP may bind to the ECM under particular binding conditions. It is possible that the ECM could facilitate the binding of 4-1BB to a specific cell-surface ligand.

B cells and helper T cells interact with each other through receptors on B cells binding to their specific counter-receptors on T cells. It is thought that this interaction results in a cascade of biochemical signaling relays between these two cell types (20). As this interaction proceeds, these cells become committed to enter the S phase of the cell cycle. Initial interactions between TCR and CD4 on T cells, and processed antigen-MHC II on B cells, do not result in B cells capable of entering the cell cycle (21). However, studies from in vitro systems suggest that once T-cells are stimulated, they express newly synthesized or modified cell-surface molecules capable of inducing B cells to enter the cell cycle (22, 23). This T-cell function is not antigen-specific or MHC-restricted (24). In addition, soluble factors are not required for the activated Th induction of B-cell activation (25). Once B cells enter the cell cycle, IL-4 induces B cells to progress from $G_1$ to S phase. The ability of activated T cells or T-cell membranes to promote the entry of B cells into the cell cycle can be blocked by either cycloheximide or cyclosporin A treatment (26, 27). These newly expressed membrane proteins appear to be "lymphokine-like" in their induction characteristics.

4-1BB has expression properties which meet the requirements of a B-cell costimulator. 4-1BB is inducible by anti-CD3 or TCR-mediated T-cell stimulation, and its expression is sensitive to cyclosporin A as well as cycloheximide treatment (28). Interestingly, paraformaldehyde-fixed SF21-4-1BB cells, synergized with anti-µ in inducing B-cell proliferation. The costimulation of splenic B cells by SF21-4-1BB occurred at optimal (10 µg/ml) and suboptimal (1.0-0.1 µg/ml) doses of anti-µ. The addition of SF21-4-1BB cells to resting B cells, did not result in significant B-cell proliferation. SF21-4-1BB cells did not synergize with TPA or ionomycin, or suboptimal concentrations of LPS in inducing B-cell proliferation.

Although the baculovirus system has been used to express large amounts of recombinant soluble proteins, this system may be utilized for the expression of recombinant cell-surface proteins. The baculovirus infection provides a convenient means to express uniformity high levels of recombinant protein on a per cell basis. It is noteworthy, that the addition of SF21 cells alone did not result in significant levels of costimulation. This can be a potential problem when using cos- or L-cell lines which can exhibit strong costimulator activity on their own.

Another member of the NGFR superfamily, CD40, is expressed on B cells and interacts with gp39, a molecule expressed on activated T cells. The cDNAs encoding the murine (29) and human (30) gp39 proteins have been cloned; this cell surface molecule is a type II membrane protein with homology to tumor necrosis factor. Noelle et al. (31) found that a CD40-immunoglobulin fusion protein, is capable of blocking T cell-induced B-cell proliferation and differentiation in a dose-dependent manner. Armitage et al. have isolated a cDNA for murine gp39 and showed that gp39 could induce B-cell proliferation in the absence of co-stimuli, and result in IgE production in the presence of IL-4-. Hollenbaugh et al. (32) have shown that COS cells transfected with human gp39 can synergize with either TPA or anti-CD20 in inducing human B-cell proliferation and is able to stimulate B cells without a costimulator only at low levels. These data indicate that CD40 may be one of the B-cell-surface molecules that transmit signals during physical contact with T cells.

Cell-surface receptors communicate with their external milieu by interacting either with soluble factors or other cell surface molecules expressed on neighboring cells. The role of biochemical signals delivered by cell-cell contact versus those delivered by soluble factors interacting with cell surface receptors is not clear. The NGFR superfamily is unusual for the TNFR I and II as well as the NGFR bind to more than one ligand. The TNFRs I and II both bind to TNF-α and TNF-R (33). The NGFR binds to NGF, brain-derived neurotrophic factor, and neurotrophin-3 (34).

In addition, one ligand may function as both a cell surface and soluble ligand. Recent evidence on the CD4-0 ligand, gp39, suggests that this ligand can exist as a membrane bound as well as a soluble ligand (35). It may be possible that 4-1BB is secreted and interacts with B cells in a soluble form as well as a membrane bound form. A member of the NGFR receptor family, CD27, which is expressed on T cells, is secreted in addition to being expressed on the cell surface (36). It is also possible that more than one 1 ligand (soluble and cell surface) may bind to 4-1BB.

Isolation of the Human Homologue, H4-1BB

In order to isolate the human homologue (H4-1BB) of mouse 4-1BB two sets of polymerase chain reaction (PCR) primers were designed. To design the PCR primers, the amino acid sequence among the members of nerve growth factor receptor (NGFR) superfamily were compared because 4-1BB is a member of the superfamily (37). The amino acid sequences employed were mouse 4-1BB (38), human NGFR (39), human tumor necrosis factor receptors (33), human CD40 (40), and human CD27 (6). The areas of sequence conservation among the NGFR superfamily were chosen.

Forward primer I (H4-1BBFI) spans from amino acids 36 to 41 and forward-primer II (HR-1BBFII) spans from amino acids 52 to 58 of the mouse 4-1BB. Reverse primer I (H4-1BBRI) spans from amino acids 116 to 121 and reverse primer II (H4-1BBRII) spans from amino acids 122 to 128 of mouse 4-1BB. The regions used as PCR primers in mouse 4-1BB are indicated if FIGS. 1a and 1b.

The degenerative oligonucleotide sequence of each primer is as follows:

```
H4-1BBFI:    5' TTC TGT CGI AAA TAT AAT CC 3'
                T   C A     G   C   C

H4-1BBFII:   5' TTC TCI TCI ATT GGI GGI CA 3'
                T   G   G   C
                            A

H4-1BBRI:    5' CC IAA IGA ACA IGT TTT ACA 3'
                   G   CT G      C   G

H4-1BBRII:   5' TT TTG ATC ATT AAA IGT ICC 3'
                   C   G   G   G
```

Peripheral blood lymphocytes from normal healthy individuals were isolated and activated with PMA (10 ng/ml) and ionomycin (1 µM). mRNA from the lymphocytes was isolated. Using reverse transcriptase the human lymphocyte mRNA was converted to single-stranded cDNA. The cDNA was then amplified with Taq polymerase with combination of the primers. The combination of primers was as follows: H4-1BBFI vs H4-1BBRI; H4-1BBFI vs H4-1BBRII; H4-1BBFII vs H4-1BBRI; and H4-1BBFII vs H4-1BBRII.

The primer set of H4-1BBFII and H4-1BBRII produced a specific band of ~240 bp. The 240 bp is an expected size of human 4-1BB if the human homologue protein is similar to mouse 4-1BB in size. The PCR product (240 bp) was cloned in PGEM3 vector and sequenced. One open reading frame of the PCR product was ~65% identical to mouse 4-1BB. Therefore, it was concluded that the 240 bp PCR product is the human homologue of mouse 4-1BB. The 240 bp PCR product was used to screen λgt11 cDNA library of activated human T lymphocytes. An ~0.85 kb cDNA was isolated. The sequence of the cDNA is shown in FIG. 2a and the predicted amino acid sequence is shown in FIG. 2b. The same information is shown is the sequence listing attached to this specification in sequence id. 1.

An expression plasmid to produce H4-1BB-AP fusion protein was constructed. The 5' portion of the H4-1BB cDNA including sequences encoding the signal sequence and the entire extracellular domain, was amplified by PCR. For correctly oriented cloning, a Hind III site on the 5' end of the forward primer and a Bgl II site on the 5' end of the reverse primer were created.

The Hind III-Bgl II H4-1BB fragment was inserted into the mammalian expression vector APtaq-1, upstream of the coding sequence for human placental alkaline phosphatase (AP). The oligonucleotides PCR primers used for the amplification of 5' portion of H4-1BB are as follows:

Forward primer: 5' AAT AAG CTT TGC TAG TAT CAT ACC T 3'

Reverse primer: 5' TTA AGA TCT CTG CGG AGA GTG TCC TGG CTC 3'

H4-1BB-AP will be used to identify cells and tissues that express ligand for human 4-1BB (i.e. H4-1BBL). The studies with mouse 4-1BB indicated that the ligand for 4-1BB is on the cell surface. B cells and macrophages were major cells that express 4-1BBL. It is expected that H4-1BBL also expresses on human B cells and macrophages.

A mammalian expression cDNA library will be generated from human cell lines that express H4-1BBL. The library will be screened by [$^{125}$I] I-labeled H4-1BB-AP. cDNA for H4-1BBL will then be isolated and characterized. Soluble recombinant H4-1BBL will then be produced. Both H4-1BB-AP and H4-1BBL will be used to suppress or enhance immune responses as described below. Monoclonal antibody to H4-1BB and H4-1BBL will be produced.

According to studies with mouse 4-1BB, 4-1BB acts as a costimulatory signal. It is expected that H4-1BB will act as a costimulatory signal for T cell activation. Mouse 4-1BB helped B cells with proliferation and differentiation. It is expected that H4-1BB will do the same. H4-1BB-AP, H4-1BBL and monoclonal antibody can be used to suppress or enhance human immune responses.

Figures 3A, 3B:
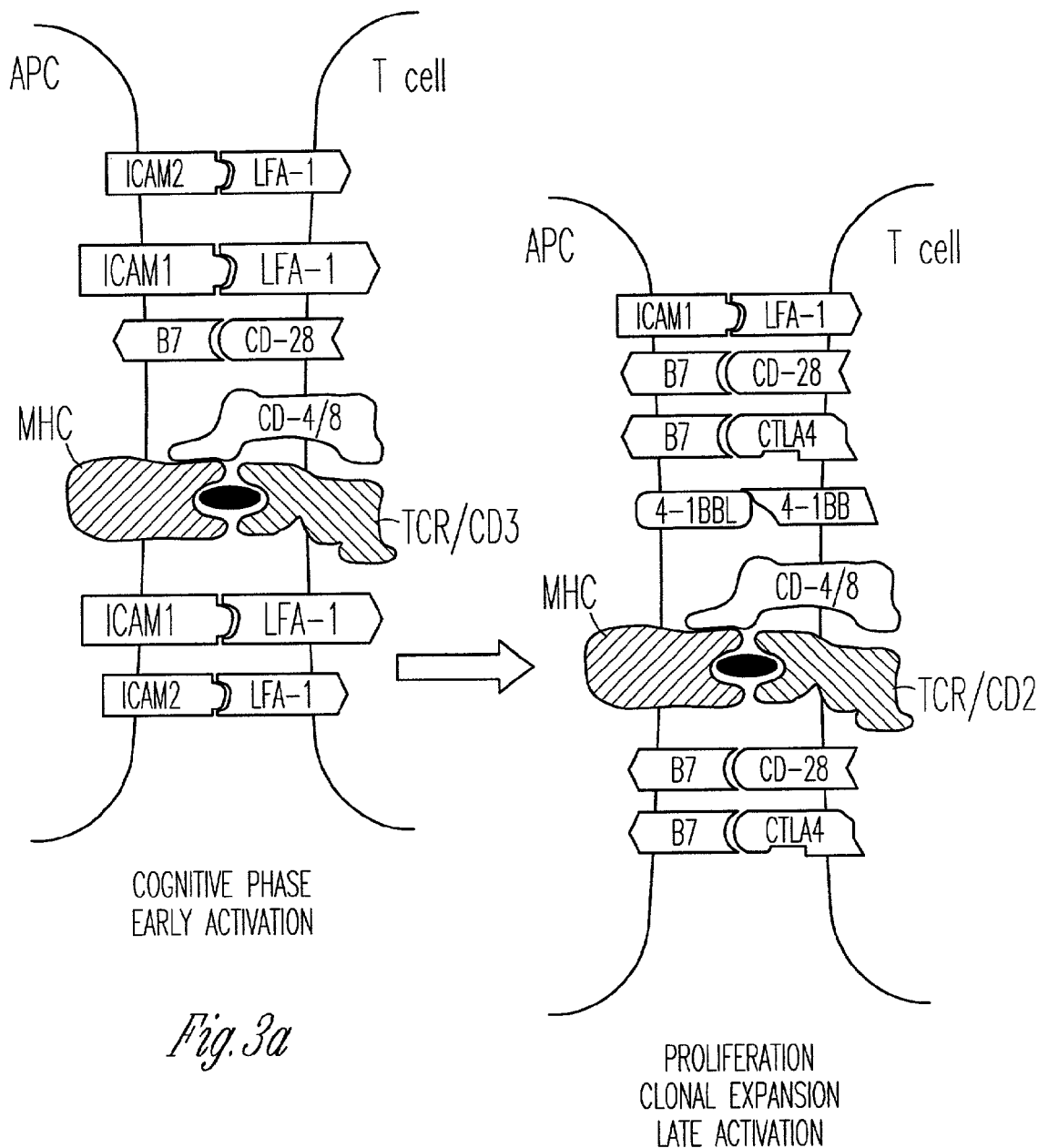
FIGS. 3a and 3b illustrate the molecules involved in T-cell activation.

FIGS. 3a and 3b illustrate the molecules involved in T-cell activation. During early T-cell activation (cognitive phase), resting T cells express the TCR/CD3 complex and other "accessory" molecules. Among these constitutively expressed molecules, CD4 (or CD8), LFA-1 and CD28 are probably the ones to receive costimulatory signals. Initial interaction with the TCR/CD3 complex in combination with these 'accessory' costimulatory signals leads to subsequent expression of additional receptor molecules such as CD28, CTLA4, and 4-1BB. These newly expressed molecules are probably going to receive additional important costimulatory signals at later stages of T-cell activation (clonal expansion).

Suppression of Immune Responses

FIGS. 4a-c illustrate a normal T-cell activation pathway. FIGS. 5a-c illustrate the blocking of immune responses with soluble chimera of 4-1BB. If 4-1BB plays a role in T-cell activation, blocking of the interaction to its ligand on antigen-presenting cells should result in suppression of T-cell dependent immune responses. It is well documented that blocking of the interaction of CD28 to its counter-receptor B7 suppresses in varying degrees, both in vivo antibody production and cell-mediated immune responses. Blocking of both interactions should result in a more effective immunosuppression; since 4-1BB is induced during T-cell activation. Blocking of the interaction of 4-1BB to its ligand may be of importance at later stages of the activation process where the CD28/B7 interaction may no longer be of relevance.

As illustrated with mouse receptor 4-1BB and mouse ligan 4-1BBL above, addition of H4-1BB-AP will coat the H4-1BBL expressing cells and block the normal interaction between H4-1BB and H4-1BBL. This will lead to immunosuppression. This type of immunosuppression is antigen-specific. Therefore it avoids the generalized immunosuppression produced by antiCD3 or cyclosporin A treatments. H4-1BB-AP treatment can be used to treat certain autoimmune diseases and to facilitate organ transplantation.

Immune Enhancement

H4-1BB may function at the late stage of T cell activation and may be a critical molecule for completion of T cell activation. Most tumors display tumor-specific antigens. One reason, however, why immunogenic tumors can escape host immunity is that tumor-reactive T cells receive inadequate costimulation. The introduction of the costimulatory molecules, such as H4-1BB into the tumor, therefore, could enhance the antitumor immunity of cytotoxic T cells (CTL). H4-1BBL can be expressed in cell-specific fashion. For example, the H4-1BBL can be expressed in melanoma using melanocyte-specific promoter such as tyrosinase promoters. The H4-1BBL-expressing melanoma will stimulate cytotoxic T cells through H4-1BB and activate the melanoma-specific CTL. The activated melanoma-specific CTL can destroy melanoma.

APPENDIX TO REFERENCES INCORPORATED BY REFERENCE

1. Smith, C. A., Davis, T., Anderson, D., Solam, L., Beckmann, M. P., Jerzy, R., Dower, S. K., Cosman, D., and Goodwin, R. G. 1990. A receptor for tumor necrosis factor defines an unusual family of cellular and viral proteins. Science 248:1019-1023.
2. Ebina, Y., L. Ellis, K. Jaruagin, M. Edery, L. Graf, E. Clauser, J. On, F. Marizrz, Y. W. Kan, J. D. Goldfine, R. A. Roth and W. J. Rutter, 1985, The human insulin receptor cDNA: the structural basis for hormone-activated transmembrane signalling, Cell 40:747.
3. Vassali, R., R. Tedghi, B. Listowska-Bernstein, A. Tartakoff and J. C. Jaton, 1979, Evidence for hydrophobic region within heavy chains of mouse B lymphocyte membrane-bound IgM, Proc. Natl. Acad. Sci. USA 76:5515.
4. Haskins, K., R. Kubo, J. White, M. Pigeon, J. Kappler and P. Marrack, 1983, The major histocompatibility complex-restricted antigen receptor on T cells I Isolation with monoclonal antibody, J. Exp. Med. 157:1149.
5. Lesslaver, W. and H. Gmunder, 1986, Biochemical characterization of the 9.3 antigens of human T-cells: simultaneous expression of disulfide-bonded 90-Kiladalton dimers and free subunits at the cell surface, Mol. Immunol. 23:271.
6. Van Lier, R., J. Borst, T. Vroom, H. Klein, P. Mourik, W. Zeijlemaker and C. Melife, 1987, Tissue distribution and biochemical and functional properties of Tp55 (CD27) a novel T cell differentiation antigen, J. Immunol. 139:1589.
7. Mallett, S., S. Fossum and A. Barclay, 1990, Characterization of the MRC OX40 antigen of activated CD4 positive T lymphocytes-a molecule related to nerve growth factor receptor, EMBO J. 9:1603.
8. Banchereau, J., P. Paoli, A., Valle, E. Garcia and F. Roussel, 1991, Long-term human B cell lines dependent on interleukin-4 and antibody to CD40, Science 251:70.
9. Moeller, D. L., M. K. Jenkins and R. H. Schwartz, 1989, Clonal expansion versus functional colonal inactivation: a co-stimulatory signalling pathway determines the outcome of T cell antigen receptor occupancy, Ann. Rev. Immunol. 7:445.
10. June, D. H., J. A. Ledbetter, P. S. Linsley and C. B. Thompson, 1989, Role of CD28 receptor in T cell activation, Immunol. Today 11:211.

11. Yang, L., B. Jones, A. Aruffo, K. M. Sullivan, P. S. Linsley and C. A. Janeeway, Jr., 1992, Heat stable antigen is a co-stimulatory molecule for CD4 T cell growth, J. Exp. Med. 175:437.
12. Yamori, T., 1992, Molecular mechanisms for generation of neural diversity and specificity: foles of polypeptide factors in development of post-mitotic neurons, Neurosic. Res. 12:545.
13. Liu, Y. J., D. E. Joshua, G. T. Williams, C. A. Smith, J. Gordon and I. C. M. MacLennan, 1989, Mechanism of antigen-driven selection in germinal centres, Nature, 342:929.
14. Jabara, H. H., s. M. Fu, R. S. Geha and D. Vercelli, 1990, CD40 and IfE: synergism between anti-CD40 monoclonal antibody and interleukin 4 in the induction of IgE synthesis by highly purified human B cells, J. Exp. Med. 172:1861.
15. Defrance, R., B. Vanbervliet, F. Briere, I. Durnad, F. Roussle and J. Banchereau, 1992, Interleukin 10 and transforming growth factor β cooperate to induce anti-CD40 activated naive human B cells to secrete immunoglobulin A, J. Exp. Med. 175:671.
16. Donahue, T., Cigan, A., Pahich, E. and Valavicius, B., Mutations at a Zn(II) finger motif in the yeast elF-2β gene alter ribosomal start-site selection during the scanning process, Cell 54 (1988) 621-632).
17. Carthew, R. W and Rubin, G. M., seven in absentia, a gene required for specification of R7 cell rate in the *Drosophila* eye, Cell, 63 (1990) 561-577.
18. Driscoll, D. M. and Williams, J. G., Two divergently transcribed genes of *Dictyostelium discoideum* are cyclic AMP-inducible and coregulated during development, Mol. and Cell. Biol. 7 (1987) 4482-4489.
19. Chalupny, N. J., Peach, R., Hollenbaugh, D., Ledbetter, J. A., Farr, A. G. and Aruffo, A., 1992, Proc. Natl. Acad. Sci USA 89:10360-10364.
20. Noelle, R. J., and Snow, E. C., 1991, The FASEB J. 5:2770-2776.
21. Noelle, R. and Snow, E., 1990, Immunol. Today 11:361-368.
22. Zurawski, G., Benedik, M., Kamb, B. J., Abrams, J. S., Zurawaki, S. M. and Lee, F. D. (1986) *Science* 232.772-775.
23. Kinachi, T. (1986) *Nature* 325,70-73.
24. Gershenfeld, H. K. and Weissman, I. L. *Science* (1986) 232, 854-858.
25. Biggin, M., Gison, T. and Hung, G. (1983 *Proc. Natl. Acad. Sci. USA* 80,3963-3965.
26. Hodgkin, P. D., Yamashita, L. C., Coffman, R. L. and Kehry, M. R., 1990, J. Immunol. 145:2025-2034.
27. Barlett, W. C., McCann, J., Shephaer, D. M., Roy, M. and Noelle, R. J., 1990, J. Immunol. 145:3956-3962.
28. Kwon, B. S., Kestler, D. P., Eshhar, Z., Oh, K., and Wakulchik, M. 1989. Expression characteristics of two potential T cell mediator genes. Cell. Immunol. 121:414-422.
29. Armitage, R., Fanslow, W., Strockbine, L., Sato, T., Clifford, K., MacDuff, B., Anderson, D., Gimpel, S., Davis-Smith, T., Maliszewski, C., Clark, E., Smith, C., Grabstein, K., Cosman, D. and Spriggs, M., 191, Nature 357:80-82.
30. Kwon, B., Kestler, D., Lee, E., Wakulchik, M. and Young J. (1988) *J. Exp. Med*) (1988) (In press).
31. Noelle, R. J., Roy, M., Shepherd, D. M., Stamenkovic, I., Ledbetter, J. A. and Aruffo, A., 1992, Proc. Natl. Acad. Sci. USA 89:6550-6554.
32. Hollenbaugh, D., Grosmaier, L. S., Kullas, C. D., Chalupny, N. J., Braesch-Andersen, S., Noelle, R. J., Stamenkovic, I., Ledbetter, J. A. and Aruffo, A., 1992, EMBO 11:4314-4321.
33. Schall, T. J., M. Lewis, K. J. Koller, A. Lee, G. C. Rice, G. H. W. Wong, T. Gatanaga, G. A. Granger, R. Lentz, H. Raab, W. J. Kohr and D. V. Goeddel, 1990, Molecular cloning and ex8pression of a receptor for human tumor necrosis factor, Cell 61:361.
34. Klein, R., Nanduri, V., Jing, S., Lamballe, F., Tapley, P., Bryant, S., Cordon-Cardo, C., Jones, K. R., Reichardt, L. F. and Barbacid, M., 1991, Cell 66:395-403.
35. Armitage, R. J., Sato, T. A., Macduff, B. M., Clifford, K. N., Alpert, A. R., Smith, C. A. and Fanslow, W. C., 1992, Eu8r. J. Immunol. 22:2071-2076.
36. Hintzen, R. Q., deJong, R., Hack, E. E., Chamuleau, M., de Vries, E. F. R., ten Berge, I. J. M., Borst, J. and van Lier, R. A. W., 1991, J. Immunol. 147:29-35.
37. Mallett, S., and Barclay, A. N. 1991. A new super-family of cell surface proteins related to the nerve growth factor receptor. Immunol. Today. 12:220-223.
38. Kwon, B. S., and Weissman, S. M. 1989. cDNA sequences of two inducible T-cell genes. Proc. Natl. Acad. Sci. USA. 86:1963-1967.
39. Johnson, D., Lanahan, A., Buck C. R., Sehgal, A., Morgan, C., Mercer, E., Bothwell, M., and Chao, M. 1986. Expression and structure of the human NGF receptor. Cell 47:545-554.
40. Stamenkovic, I., Clark, E., and Seed, B. 1989. A B-lymphocyte activation molecule related to the nerve growth factor receptor and induced by cytokines in carcinomas. EMBO. J. 8:1403-1408.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

I claim:

1. An isolated nucleic acid molecule having a nucleotide sequence comprising SEQ ID NO: 1, wherein the nucleic acid molecule encodes an extracellular domain of a human receptor protein H4-1BB.

2. The isolated nucleic acid molecule of claim 1, identified as pH4-1BB deposited at the Agricultural Research Service Culture Collection with the accession number NRRL B21131.

3. An isolated nucleic acid molecule comprising a nucleotide sequence that encodes the extracellular domain of a human receptor protein H4-1BB of SEQ ID NO:2 and wherein said nucleic acid molecule comprises nucleotides 41-805 of SEQ ID NO:1 or nucleotides 41-598 of SEQ ID NO:1.

4. A recombinant expression vector comprising the nucleic acid molecule of claim 3 operably linked to regulatory sequences suitable for expression of the nucleic acid molecule in a host cell.

* * * * *

UNITED STATES PATENT AND TRADEMARK OFFICE
CERTIFICATE OF CORRECTION

PATENT NO. : 8,026,353 B2  
APPLICATION NO. : 10/027199  
DATED : September 27, 2011  
INVENTOR(S) : Byoung Se Kwon It is certified that error appears in the above-identified patent and that said Letters Patent is hereby corrected as shown below:

Column 1, please delete the second paragraph (lines 10-14) and insert the following therefor:

--GOVERNMENT RIGHTS

This invention was made with government support under AI28175, AI23058 and KD20542 awarded by the National Institutes of Health. The U.S. Government has certain rights in the invention.--

Signed and Sealed this
Thirty-first Day of January, 2012

David J. Kappos
*Director of the United States Patent and Trademark Office*

SEQUENCE LISTING

```
<160> NUMBER OF SEQ ID NOS: 12

<210> SEQ ID NO 1
<211> LENGTH: 838
<212> TYPE: DNA
<213> ORGANISM: Homo sapiens

<400> SEQUENCE: 1
aatcagcttt gctagtatca tacctgtgcc agatttcatc atgggaaaca gctgttacaa    60
```

-continued

```
catagtagcc actctgttgc tggtcctcaa ctttgagagg acaagatcat gcaggatcc      120 ttgtagtaac tgcccagctg gtacattctg tgataataac aggaatcaga tttgcagtcc    180
ctgtcctcca aatagtttct ccagcgcagg tggacaaagg acctgtgaca tatgcaggca    240
gtgtaaaggt gttttcagga ccaggaagga gtgttcctcc accagcaatg cagagtgtga    300
ctgcactcca gggtttcact gcctgggggc aggatgcagc atgtgtgaac aggattgtaa    360
acaaggtcaa gaactgacaa aaaaaggttg taaagactgt tgctttggga catttaacga    420
tcagaaacgt ggcatctgtc gaccctggac aaactgttct ttggatggaa agtctgtgct    480
tgtgaatggg acgaaggaga gggacgtggt ctgtggacca tctccagctg acctctctcc    540
gggagcatcc tctgtgaccc cgcctgcccc tgcgagagag ccaggacact ctccgcagat    600
catctccttc tttcttgcgc tgacgtcgac tgcgttgctc ttcctgctgt tcttcctcac    660
gctccgtttc tctgttgtta acggggcag aaagaaactc ctgtatatat tcaaacaacc     720
atttatgaga ccagtacaaa ctactcaaga ggaagatggc tgtagctgcc gatttccaga    780
agaagaagaa ggaggatgtg aactgtgaaa tggaagtcaa tagggctgtt gggacttt     838
```

<210> SEQ ID NO 2
<211> LENGTH: 255
<212> TYPE: PRT
<213> ORGANISM: Homo sapiens

<400> SEQUENCE: 2

```
Met Gly Asn Ser Cys Tyr Asn Ile Val Ala Thr Leu Leu Val Leu
  1               5                  10                  15

Asn Phe Glu Arg Thr Arg Ser Leu Gln Asp Pro Cys Ser Asn Cys Pro
                 20                  25                  30

Ala Gly Thr Phe Cys Asp Asn Asn Arg Asn Gln Ile Cys Ser Pro Cys
             35                  40                  45

Pro Pro Asn Ser Phe Ser Ser Ala Gly Gly Gln Arg Thr Cys Asp Ile
         50                  55                  60

Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                 85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
```

245    250    255

<210> SEQ ID NO 3
<211> LENGTH: 20
<212> TYPE: DNA
<213> ORGANISM: Homo sapiens

<400> SEQUENCE: 3
ttytgymgaa artayaaycc                                         20

<210> SEQ ID NO 4
<211> LENGTH: 20
<212> TYPE: DNA
<213> ORGANISM: Homo sapiens

<400> SEQUENCE: 4
ttytcstsca htggtggaca                                         20

<210> SEQ ID NO 5
<211> LENGTH: 20
<212> TYPE: DNA
<213> ORGANISM: Homo sapiens

<400> SEQUENCE: 5
cccargswrc aggtyttrca                                         20

<210> SEQ ID NO 6
<211> LENGTH: 20
<212> TYPE: DNA
<213> ORGANISM: Homo sapiens

<400> SEQUENCE: 6
ttytgrtcrt traatgttcc                                         20

<210> SEQ ID NO 7
<211> LENGTH: 25
<212> TYPE: DNA
<213> ORGANISM: Homo sapiens

<400> SEQUENCE: 7
aataagcttt gctagtatca tacct                                   25

<210> SEQ ID NO 8
<211> LENGTH: 30
<212> TYPE: DNA
<213> ORGANISM: Homo sapiens

<400> SEQUENCE: 8
ttaagatctc tgcggagagt gtcctggctc                              30

<210> SEQ ID NO 9
<211> LENGTH: 2350
<212> TYPE: DNA
<213> ORGANISM: Mus musculus
<220> FEATURE:
<221> NAME/KEY: unsure
<222> LOCATION: (1253)...(1255)
<223> OTHER INFORMATION: (a or g or c or t/u)

<400> SEQUENCE: 9
atgtccatga actgctgagt ggataaacag cacgggatat ctctgtctaa aggaatatta    60
ctacaccagg aaaaggacac attcgacaac aggaaaggag cctgtcacag aaaaccacag   120
tgtcctgtgc atgtgacatt tcgccatggg aaacaactgt tacaacgtgg tggtcattgt   180

```
gctgctgcta gtgggctgtg agaaggtggg agccgtgcag aactcctgtg ataactgtca    240
gcctggtact ttctgcagaa aatacaatcc agtctgcaag agctgccctc caagtacctt    300
ctccagcata ggtggacagc cgaactgtaa catctgcaga gtgtgtgcag gctatttcag    360
gttcaagaag ttttgctcct ctacccacaa cgcggagtgt gagtgcattg aaggattcca    420
ttgcttgggg ccacagtgca ccagatgtga aaaggactgc aggcctggcc aggagctaac    480
gaagcagggt tgcaaaacct gtagcttggg aacatttaat gaccagaacg gtactggcgt    540
ctgtcgaccc tggacgaact gctctctaga cggaaggtct gtgcttaaga ccgggaccac    600
ggagaaggac gtggtgtgtg acccccctgt ggtgagcttc tctcccagta ccaccatttc    660
tgtgactcca gagggaggac caggagggca ctccttgcag gtccttacct tgttcctggc    720
gctgacatcg gctttgctgc tggccctgat cttcattact ctcctgttct ctgtgctcaa    780
atggatcagg aaaaaattcc cccacatatt caagcaacca tttaagaaga ccactggagc    840
agctcaagag gaagatgctt gtagctgccg atgtccacag gaagaagaag gaggaggagg    900
aggctatgag ctgtgatgta ctatcctagg agatgtgtgg gccgaaaccg agaagcacta    960
ggaccccacc atcctgtgga acagcacaag caaccccacc accctgttct tacacatcat   1020
cctagatgat gtgtgggcgc gcacctcatc caagtctctt ctaacgctaa catatttgtc   1080
tttacctttt ttaaatcttt ttttaaattt aattttatg tgtgtgagtg ttttgcctgc    1140
ctgtatgcac acgtgtgtgt gtgtgtgt gtgacactcc tgatgcctga ggaggtcaga    1200
agacaaaggg ttggttccat aagaactgga gttatggatg ctgtgagcc ggnnngatag    1260
gtcgggacgg agacctgtct tcttatttta acgtgactgt ataataaaaa aaaaatgata   1320
tttcgggaat tgtagagatt gtcctgacac ccttctagtt aatgatctaa gaggaattgt   1380
tgatacgtag tatactgtat atgtgtatgt atatgtatat gtatatataa gactcttta    1440
ctgtcaaagt caacctagag tgtctggtta ccaggtcaat tttattggac attttacgtc   1500
acacacacac acacacacac acacacacgt ttatactacg tactgttatc ggtattctac   1560
gtcatataat gggatagggt aaaaggaaac caaagagtga gtgatattat tgtggaggtg   1620
acagactacc ccttctgggt acgtagggac agacctcctt cggactgtct aaaactcccc   1680
ttagaagtct cgtcaagttc ccggacgaag aggacagagg agacacagtc gaaaagtta    1740
ttttttccggc aaatcctttc cctgtttcgt gacactccac cccttgtgga cacttgagtg   1800
tcatccttgc gccggaaggt caggtggtac ccgtctgtag gggcggggag acagagccgc   1860
gggggagcta cgagaatcga ctcacagggc gccccgggct tcgcaaatga aacttttta    1920
atctcacaag tttcgtccgg gctcggcgga cctatggcgt cgatccttat taccttatcc   1980
tggcgccaag ataaaacaac caaaagcctt gactccggta ctaattctcc ctgccggccc   2040
ccgtaagcat aacgcggcga tctccacttt aagaacctgg ccgcgttctg cctggtctcg   2100
ctttcgtaaa cggttcttac aaaagtaatt agttcttgct ttcagcctcc aagcttctgc   2160
tagtctatgg cagcatcaag gctggtattt gctacggctg accgctacgc cgccgcaata   2220
agggtactgg gcgcccgtc gaaggcccctt tggtttcaga acccaaggc cccctcata    2280
ccaacgtttc gactttgatt cttgccggta cgtggtggtg ggtgccttag ctcttctcg    2340
atagttagac                                                         2350

<210> SEQ ID NO 10
<211> LENGTH: 256
<212> TYPE: PRT
<213> ORGANISM: Mus musculus
```

<400> SEQUENCE: 10

```
Met Gly Asn Asn Cys Tyr Asn Val Val Ile Val Leu Leu Leu Val
  1               5                  10                  15

Gly Cys Glu Lys Val Gly Ala Val Gln Asn Ser Cys Asp Asn Cys Gln
             20                  25                  30

Pro Gly Thr Phe Cys Arg Lys Tyr Asn Pro Val Cys Lys Ser Cys Pro
             35                  40                  45

Pro Ser Thr Phe Ser Ser Ile Gly Gly Gln Pro Asn Cys Asn Ile Cys
 50                  55                  60

Arg Val Cys Ala Gly Tyr Phe Arg Phe Lys Lys Phe Cys Ser Ser Thr
 65                  70                  75                  80

His Asn Ala Glu Cys Glu Cys Ile Glu Gly Phe His Cys Leu Gly Pro
                 85                  90                  95

Gln Cys Thr Arg Cys Glu Lys Asp Cys Arg Pro Gly Gln Glu Leu Thr
                100                 105                 110

Lys Gln Gly Cys Lys Thr Cys Ser Leu Gly Thr Phe Asn Asp Gln Asn
            115                 120                 125

Gly Thr Gly Val Cys Arg Pro Trp Thr Asn Cys Ser Leu Asp Gly Arg
130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
            180                 185                 190

Leu Thr Ser Ala Leu Leu Leu Ala Leu Ile Phe Ile Thr Leu Leu Phe
            195                 200                 205

Ser Val Leu Lys Trp Ile Arg Lys Lys Phe Pro His Ile Phe Lys Gln
210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Gly Tyr Glu Leu
                245                 250                 255
```

<210> SEQ ID NO 11
<211> LENGTH: 24
<212> TYPE: PRT
<213> ORGANISM: Homo sapiens
<220> FEATURE:
<221> NAME/KEY: ZN_FING
<222> LOCATION: 2...3, 5...13, 15...17, 19...21, 23
<223> OTHER INFORMATION: Putative zinc finger structure

<400> SEQUENCE: 11

```
Cys Xaa Xaa Cys Xaa Xaa Xaa Xaa Xaa Xaa Xaa Xaa Cys Xaa Xaa
  1               5                  10                  15

Xaa His Xaa Xaa Xaa Cys Xaa Cys
                 20
```

<210> SEQ ID NO 12
<211> LENGTH: 12
<212> TYPE: PRT
<213> ORGANISM: Homo sapiens

<400> SEQUENCE: 12

```
Leu Gln Asp Pro Cys Ser Asn Cys Pro Ala Gly Thr
  1               5                  10
```